(12) United States Patent
Ott et al.

(10) Patent No.: US 10,406,301 B2
(45) Date of Patent: Sep. 10, 2019

(54) FAIL-SAFE INSUFFLATORS

(71) Applicants: Douglas E Ott, Macon, GA (US);
Steven Williams, St. Paul, MN (US);
Nathanial Tran, Lakeville, MN (US)

(72) Inventors: Douglas E Ott, Macon, GA (US);
Steven Williams, St. Paul, MN (US);
Nathanial Tran, Lakeville, MN (US)

(73) Assignee: LEXION MEDICAL, LLC, St. Paul, MN (US)

( * ) Notice: Subject to any disclaimer, the term of this patent is extended or adjusted under 35 U.S.C. 154(b) by 1006 days.

(21) Appl. No.: 13/694,689

(22) Filed: Dec. 24, 2012

(65) Prior Publication Data

US 2014/0180198 A1   Jun. 26, 2014

(51) Int. Cl.
*A61M 13/00* (2006.01)
*A61B 17/34* (2006.01)

(52) U.S. Cl.
CPC ....... *A61M 13/003* (2013.01); *A61B 17/3474* (2013.01); *A61M 2205/18* (2013.01); *A61M 2205/3368* (2013.01); *A61M 2205/3653* (2013.01); *A61M 2205/75* (2013.01)

(58) Field of Classification Search
CPC ............ A61M 113/003; A61M 113/13; A61M 2205/3368; A61M 2205/3653; A61M 2205/75; A61M 2205/18; A61M 13/00; A61M 13/003; A61M 13/08; A61B 17/3474; H01H 37/32
USPC ............................................. 604/24; 337/298
See application file for complete search history.

(56) References Cited

U.S. PATENT DOCUMENTS

| | | | |
|---|---|---|---|
| 4,189,698 A * | 2/1980 | Hara .................... | H01H 71/205 337/407 |
| 4,808,960 A * | 2/1989 | Nixon .................... | H01H 61/02 337/102 |
| 4,837,547 A * | 6/1989 | Nixon .................... | H01H 37/76 337/398 |
| 5,411,474 A | 5/1995 | Ott | |
| 6,010,118 A | 1/2000 | Milewicz | |
| 6,814,714 B1 | 11/2004 | Novak | |
| 2003/0189037 A1* | 10/2003 | Kochman .............. | H05B 3/342 219/549 |
| 2004/0102731 A1 | 5/2004 | Blackhurst | |
| 2004/0254524 A1 | 12/2004 | Spearman | |
| 2005/0113797 A1 | 5/2005 | Ott | |
| 2006/0129098 A1 | 6/2006 | Hart | |
| 2007/0088274 A1 | 4/2007 | Stubbs | |
| 2007/0088275 A1 | 4/2007 | Stearns | |
| 2008/0119833 A1* | 5/2008 | Vancelette ............. | A61B 18/02 606/20 |
| 2010/0168502 A1* | 7/2010 | Delaporte .............. | A61G 11/00 600/22 |
| 2010/0241061 A1* | 9/2010 | Ott ..................... | A61B 17/3474 604/26 |

(Continued)

*Primary Examiner* — Imani N Hayman
*Assistant Examiner* — Tiffany Legette
(74) *Attorney, Agent, or Firm* — Johnson & Phung LLC

(57) ABSTRACT

A fail-safe insufflation device having a thermal cutoff for interrupting power to an electrical heater to prevent overheating of insufflation gas wherein the thermal cutoff operates independent of a temperature control system to provide electrical shutdown of an electrical heater in response to a hostile temperature condition of the insufflation gas or a hostile temperature condition proximate the electrical heater.

19 Claims, 5 Drawing Sheets

(56) References Cited

U.S. PATENT DOCUMENTS

2011/0040247 A1\* 2/2011 Mandro ................ A61M 5/142
  604/66
2011/0064978 A1\* 3/2011 McGahan .......... A61B 17/7091
  429/61

\* cited by examiner

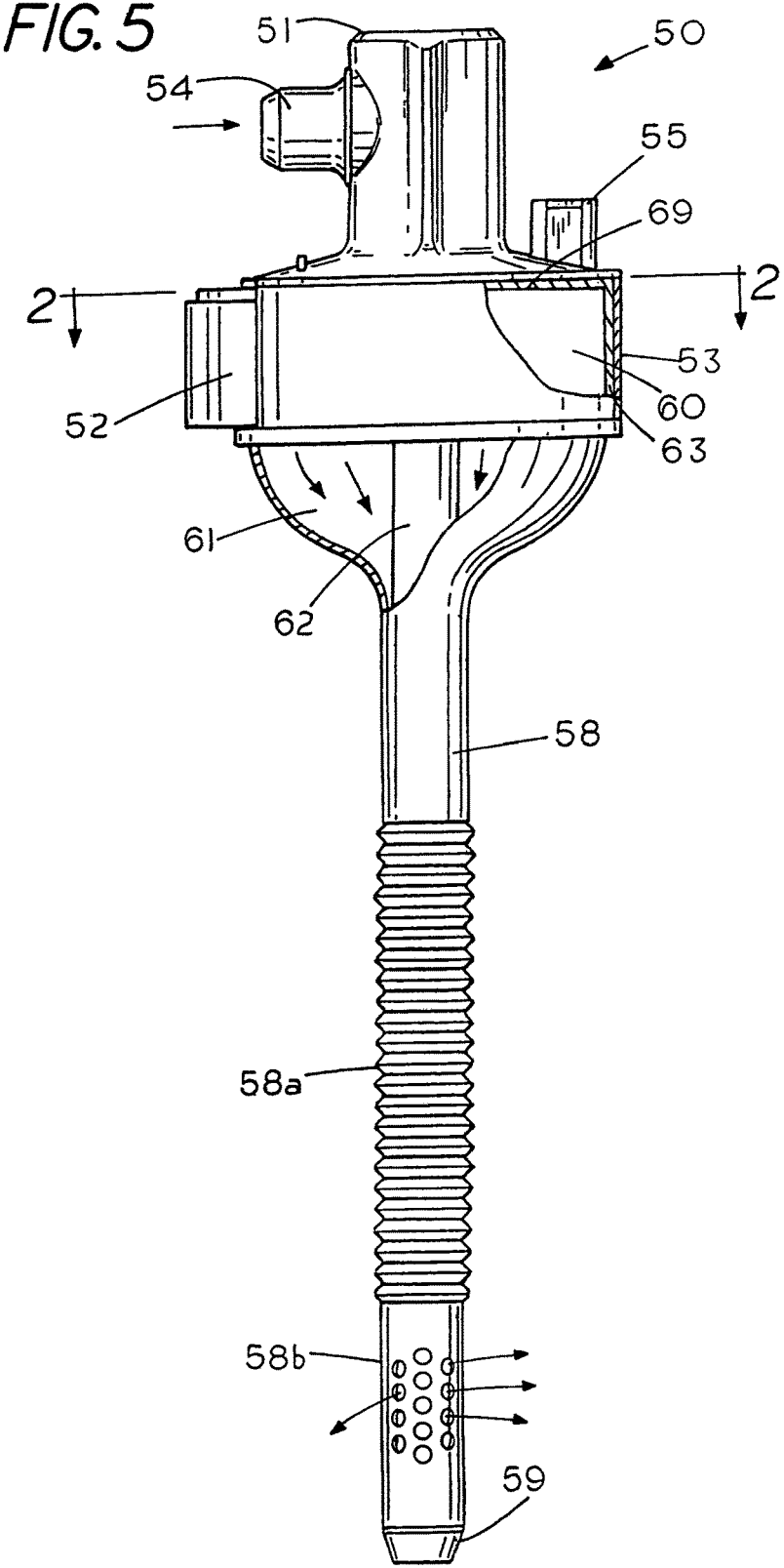

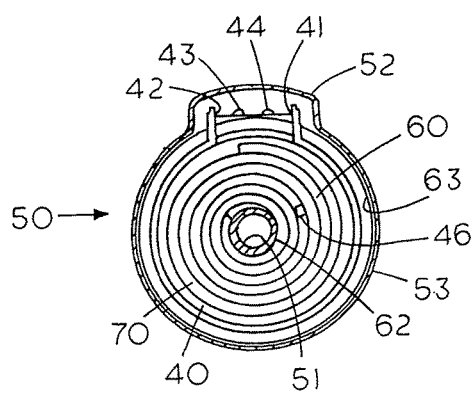
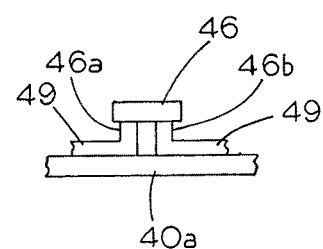
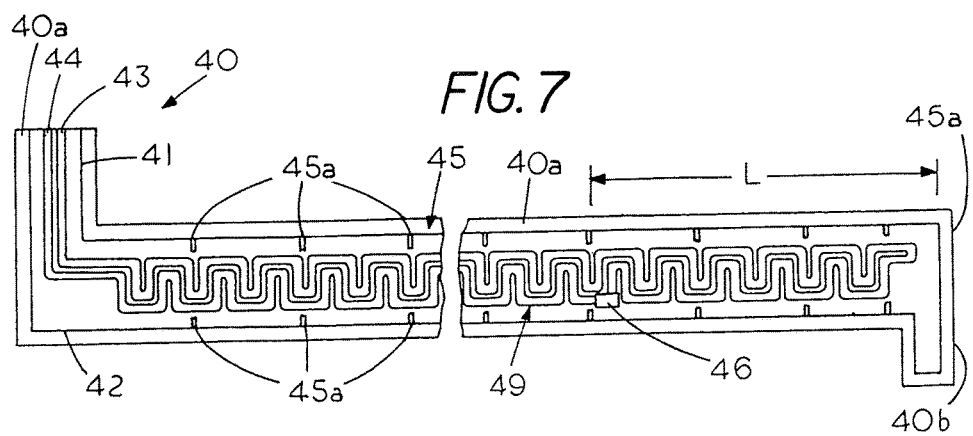
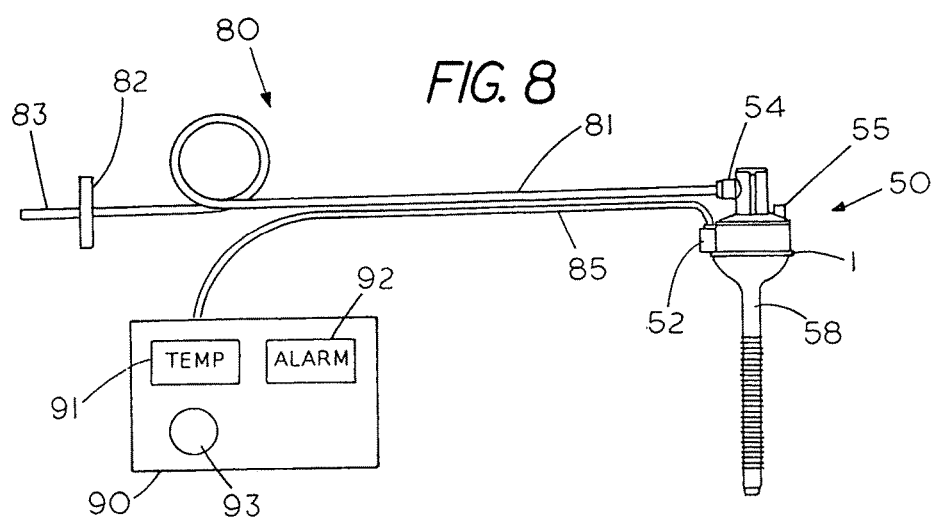

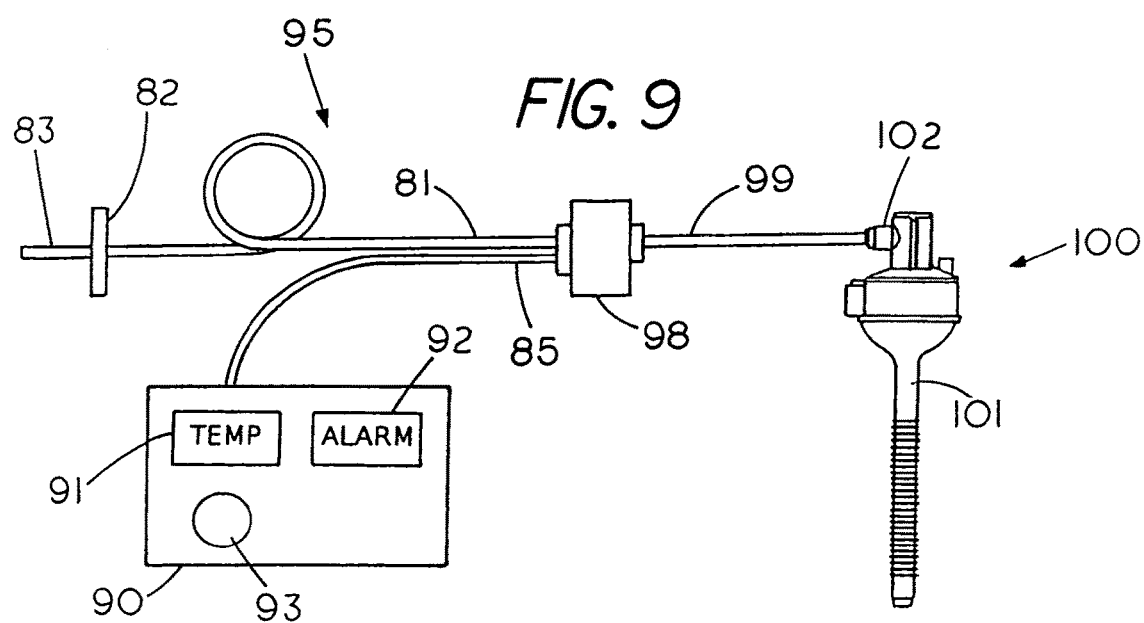

FAIL-SAFE INSUFFLATORS

CROSS REFERENCE TO RELATED APPLICATIONS

This application is a continuation in part of U.S. patent application Ser. No. 12/381,978 filed Mar. 18, 2009.

STATEMENT REGARDING FEDERALLY SPONSORED RESEARCH OR DEVELOPMENT

None

REFERENCE TO A MICROFICHE APPENDIX

None

BACKGROUND OF THE INVENTION

Generally, insufflation gas is conditioned i.e. heated and hydrated in apparatuses that are located upstream of the trocar. There are advantages to having the gas conditioning apparatus upstream of the trocar including the ability to isolate the hydration apparatus from the trocar thereby allowing one to maintain a small profile trocar for ease in handling and manipulating by a surgeon. A further benefit of upstream conditioning is that if the insufflation gas should be accidentally overheated the mass of the trocar and the mass of the connecting tubing and fittings tend to absorb excess heat thereby acting as a thermal sink to limit the temperature of the gas before it enters a patient, which reduces the chances that overheated insufflation gas may enter the patient. However, a benefit of the gas conditioning trocar is that the insufflation gas can be heated and hydrated immediately before entering a patient thus minimizing cooling of the heated insufflation gas during the enter into the patient. The source of conditioned gas closer to the patient also permits more accurate control of the temperature and humidity of the insufflation gas as it enters the body cavity since the opportunity for gas cooling is minimized. The minimizing of cooling of the insufflation gas also minimizes or eliminates a problem of moisture condensation in the insufflation gas, which may occur as a result of the insufflation gas cooling on its path into the body cavity of a patient. However in either case the temperature of the insufflation gas is typically maintained by a feedback system that measures the temperature of the gas and adjusts the heat input based on the existing temperature.

The location of the heating and hydration of the insufflation gas either within a trocar or proximate a trocar minimizes problems of condensation and gas cooling. However, other trocar operating concerns may arise since the heating and hydration control of the insufflation gas may occur in close proximity to the patient and in some cases immediately after the insufflation gas has been heated and hydrated. In some cases a failure of the temperature control system may lead to overheated insufflation gas being injected into a patient.

SUMMARY OF THE INVENTION

A fail-safe insufflator having the capacity to shutdown or interrupt power to an electrical insufflator heater in the event of a hostile temperature condition within the insufflator to thereby prevent overheating the insufflation gas therein. The insufflator may normally operate in a normal electrical shutdown mode where an electrical fault signal generated by either a thermistor or a temperature control system interrupts or controls power to the electrical heater or in a fail-safe mode where a mechanical shutdown of the electrical heater occurs in response to an excess temperature proximate the electrical heater where the excess temperature may not be an excess temperature of the insufflation gas.

BRIEF DESCRIPTION OF THE DRAWINGS

FIG. 5 is a front view of a fail-safe insufflator in a gas conditioning trocar;

FIG. 6 is a sectional view taken along lines 2-2 of FIG. 5;

FIG. 7 is a plane view of the electrical heater with a thermistor circuit and a thermal cutoff;

FIG. 7A is an isolated view of a thermal cutoff connected to an electrical heater;

FIG. 8 is a system for interrupting power to an electrical heater in response to a hostile temperature proximate the heater with the fail-safe insufflator located in a gas conditioning trocar; and FIG. 9 is a system for interrupting power to an electrical heater in response to a hostile temperature proximate the heater with the fail-safe insufflator located upstream of a trocar.

DESCRIPTION OF THE PREFERRED EMBODIMENT

Figure 1:
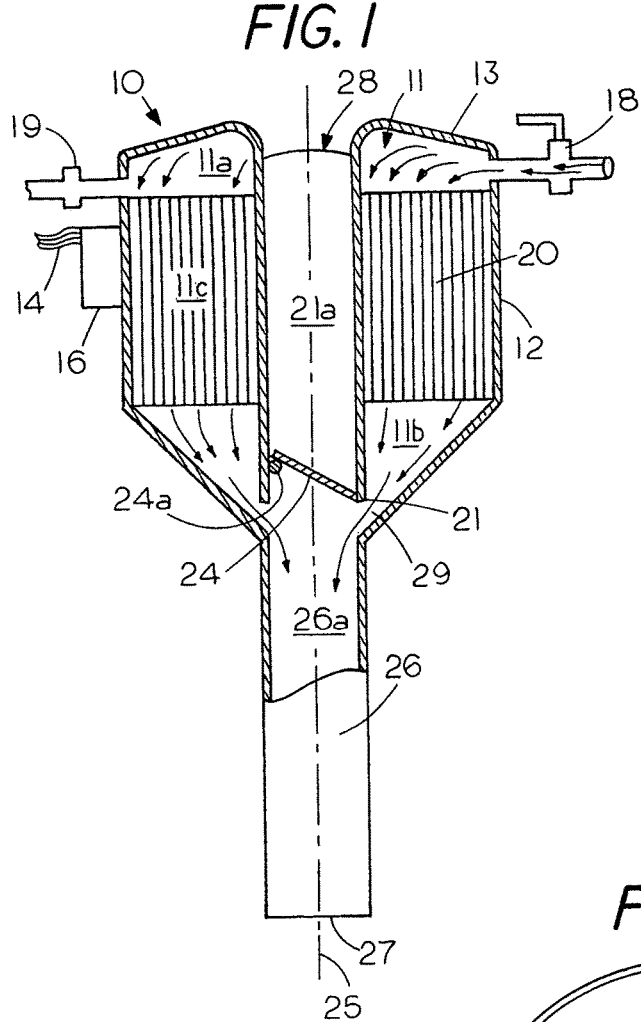
FIG. 1 is a side partial sectional view of a trocar.

FIGS. 1-4A show a gas conditioning trocar for heating and hydrating an insufflation gas within a trocar, and FIGS. 5-8 show a fail-safe insufflator for heating and hydrating an insufflation gas within a trocar. FIG. 9 shows a system for interrupting power to an electrical heater in response to a hostile temperature proximate the heater with the fail-safe insufflator located upstream of a trocar.

The insufflator systems of FIG. 1-8 use an electrical heater located within the trocar to heat the insufflation gas although the invention described herein may also be used with an electrical heater and or gas conditioning media that is separate from the trocar and is located upstream of the trocar as shown in FIG. 9. The gas conditioning trocar of FIGS. 1-4A differs from the gas conditioning trocar of FIGS. 5-8 as the latter system operates in a fail-safe inflation mode since it includes both an electrical control mode and a mechanical shutdown mode to prevent overheating the insufflation gas.

In the conventional electrical shutdown mode, a temperature sensor, which is located within the trocar, generates an electrical signal that controls the electrical power to the electrical heater within the trocar. Typically, a processor within a control station can control or interrupt power to the electrical heater if the insufflation gas becomes overheated. This type of feedback system is effective in controlling or maintaining the temperature of the insufflation gas to prevent overheating of the insufflation gas when the temperature sensor and controls are in good working order, however, if the temperature sensor or other electrical components of the system should fail the insufflation gas may become overheated. In the fail-safe insufflation mode of the system of FIG. 6 to FIG. 8 a mechanical switch, normally a passive device, within the gas conditioning media interrupts power to the electrical heater based on a temperature condition proximate the electrical heater. The fail-safe insufflation mode is a mechanical operational mode that is responsive to a temperature condition at the electrical heater and is independent of electrical system failures in other parts the system. Thus, the system is a dual mode system having a passive device, a thermal cutoff, to prevent overheating insufflation gas in the event of a failure of system components such as the temperature sensor or temperature controls in other parts of the system.

FIG. 5 is a front view, partially in section, of the fail-safe insufflator comprising a gas conditioning trocar 50 having a passive device for mechanical interruption of power to an electrical heater therein. Gas conditioning trocar 50 contains a housing 53 having an electrical port 52, a hydration port 55 for supplying hydration fluid and an insufflation gas port 54 for delivery of insufflation gas to an upper inlet plenum chamber 69. A top annular extension 51 forms an instrument port 51 that include a cylindrical instrument tube 62 that extends through cannula 58 to enable the insertion of surgical instruments therethrough as well as the manipulation of the surgical instruments within the body cavity of a patient. In the example shown the instrument tube 62 and the cannula 58 are located in a concentric relationship forming an annular passage 61 therebetween that directs a conditioned insufflation gas through the cannula annular passage 61, the radial gas ports 58b and into the body cavity of a patient. Cannula 58 also includes a set of external, anti-removal, annular serrations 58a, which are located above insufflation ports 58b, to assist in anchoring the trocar to the body of the patient. Located at the distal end of the cannula 58 is a tapered annular lip 59 for insertion of the cannula through the body tissue of a patient.

Figure 4:
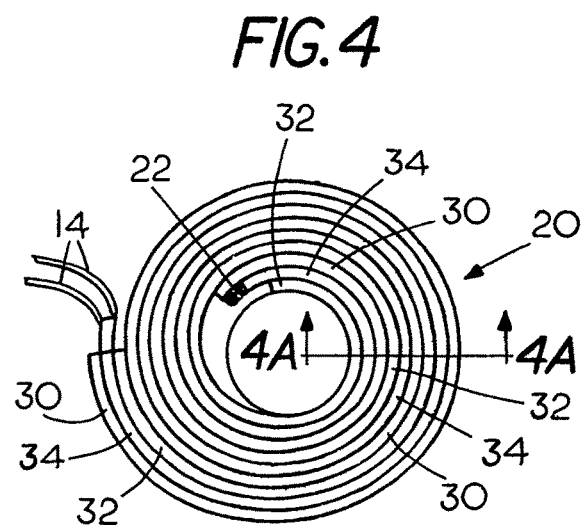
FIG. 4 is top view of the multilayer media arranged in a spiral configuration.
Figure 4A:
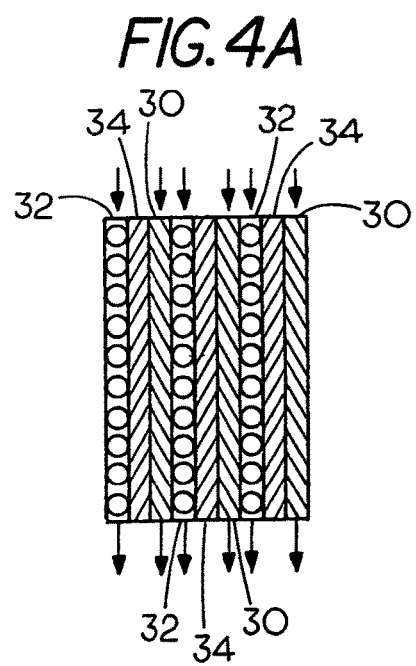
FIG. 4A is a cross sectional view taken along lines 4A-4A of FIG. 4.

Gas conditioning trocar 50 includes an annular chamber 63 containing a spiral wound gas conditioning media 60 for heating and hydrating insufflation gas as it flows through the gas conditioning trocar. An example of a gas conditioning media having an electrical heater therein is shown in FIG. 4 and FIG. 4a.

FIG. 6 is a sectional view taken along lines 2-2 of FIG. 5 revealing the spiral wound conditioning media 60 located within the annular chamber 63 with the annular chamber 63 centrally defined by an instrument tube 62. A Cylindrical side wall 51 on the interior of instrument tube 61 defines a cylindrical passage for receiving and manipulating medical instruments therein. The electrical hub or port 52, includes electrical heater leads 43 and 44 as well as thermistor circuit leads 41 and 42. In the example shown the gas conditioning media 60, which includes a hydration member 70 and an electrical heater 40 are typically located in a face to face condition as insufflation gas flows axially along a side of the electrical heater and a side of the hydration member to heat and hydrate the insufflation gas.

FIG. 7 shows a plane view of the electrical heating strip 40 for on-the-go heating of the hydration fluid within the annular chamber 63 of the gas conditioning trocar 50. The electrical heating strip 40, which is spiral wound within the media 60 typically includes an electrically insulating backing strip 40a that supports a thermistor circuit 45 having a set of thermistors 45a responsive to a temperature of the insufflation gas flowing therepast. The thermistor circuit 45 contains a set of thermistors 45a that are connected in series and are located on opposite edges of the electrical heating strip 40. Thermister circuit leads 41 and 42, which are connectable to an external power source also connect to an electrical heating element 49 that extends in a series of back and forth U shaped pattern along an interior portion of the heating strip 40 from the heating strip's proximal end to the distal end 40b. Application of electrical power to electrical heating element 49 heats the insufflation gas as it flows therepast while the change in resistance of the thermistors 45 provides an on-the-go indication of the temperature of the insufflation gas as it flows past the heating strip 40.

FIG. 8 shows an example of a hydration control system 80 having a flexible tube 83 for connecting to a source of unconditioned or unheated insufflation gas, a gas filter 82 for removing unwanted particles from the insufflation gas and a further flexible tube 81 with the tubes typically made from a medical grade PVC. Tube 81 connects to inlet gas port 54 on the gas conditioning trocar 50 to deliver the unconditioned insufflation gas to the trocar 50. Extending outward from the gas conditioning trocar 50 is an electrical port 52, which contains leads 42, 41, 44 and 43 from heating strip 40 with the leads in electrical communication with control station 90 through a flexible electrical cable 85. Control station 90 includes a processor (not shown), a visual temperature readout 91 and an alarm 92, which may be a visual alarm—or an audible alarm or both. A control knob 93 allows one to select the temperature of the insufflation gas to be delivered to the patient. Once the temperature is set a feedback circuit within the control station 90 automatically increases or decreases the power to the electrical heater 40 to maintain the insufflation gas at the proper temperature.

If the temperature of the insufflation gas exceeds a safe level for patient insertion the thermistor circuit 45 generates an electrical signal causing the processor in control station 90 to automatically decrease the power to the heating element 49 based on the electrical signal generated by the thermistor circuit 45. Thus, the temperature of the insufflation gas delivered from a gas conditioning trocar can be automatically maintained or controlled by a processor in the control station. On the other hand, unexpected conditions may cause the insufflation gas to be overheated. For example, an electrical failure in the thermistor circuit 45 or in the control station 90 may allow the insufflation gas to exceed a safe temperature. The system described herein utilizes a passive device, which is thermally sensitive, to prevent overheating the insufflation gas in the event an electrical or temperature measurement failure does not interrupt power to the electrical heater.

FIG. 9 shows a system 95 for interrupting power to an electrical heater in response to a hostile temperature proximate the heater with the fail-safe insufflator located upstream and outside of a trocar. The system 95 is similar to the system of FIG. 8 and includes a flexible tube 83 for connecting to a source of unconditioned or unheated insufflation gas, a gas filter 82 for removing unwanted particles from the insufflation gas and a further flexible tube 81 with the tubes typically made from a medical grade PVC. Tube 81 connects to a fail-safe insufflation device 98 that conditions insufflation gas for delivery to the trocar 100 through tubing 99. Extending outward from the fail-safe insufflator device 98 and in electrical communication with control station 90 is a flexible electrical cable 85. Control station 90 includes a processor (not shown), a visual temperature readout 91 and an alarm 92, which may be a visual alarm or an audible alarm or both. A control knob 93 allows one to select the temperature of the insufflation gas to be delivered to the patient. Once the temperature is set a feedback circuit within the control station 90 automatically increases or decreases the power to the electrical heater within the insufflator device 98 to maintain the insufflation gas at the proper temperature.

A reference to FIG. 7 shows a passive device 46 located on a leg of the heating element 49 a well as in series with the heating element 49. The passive device 46 comprises a thermal cutoff that is positioned so as to be responsive to the temperature proximate the heating element 49, which is located in a chamber for heating the insufflation gas. The thermal cutoff differs from a fuse in that the thermal cutoff interrupts power to a device when the thermal cutoff is heated to a specific temperature. A temperature having a thermal cutoff temperature of about 102 C provides a system that inhibits or avoids presenting overheated insufflation gas to a body cavity of a patient although the cutoff temperature may be higher or lower depending on the location and the type of system. FIG. 7A shows an isolated view of thermal cutoff 46 having a first lead 46a that connects to one end of heating element 49 and a second lead 46b that connects to another end of heating element 49. In normal system operation current flows through the heating element 49 and the thermal cutoff 46. Normally, if the temperature of the insufflation gas exceeds a safe level the control station 90 (FIG. 8) generates an electrical signal that decreases or shuts down the power to the heating element 49. On the other hand if an electrical system failure occurs, which is not detected by the thermistor circuit 45 or the control station 90, it may cause the temperature of the insufflation gas to exceed a safe temperature since power may continue to be supplied to the electrical heater. Since the system described herein includes a passive device, i.e. a thermal cutoff 46, located proximate the electrical heater power to interrupt power to the electrical heater, which may be due an errant temperature condition proximate, the electrical heater rather than a sensed temperature of the insufflation gas. That is the systems operates in a fail-safe insufflation mode since the system responds to an increase in the temperature of the passive device exceeding a fixed temperature which mechanically opens the electrical conducting path from lead 46a to 46b (FIG. 7A) thus interrupting electrical power to the electrical heating element 49, which prevents overheating of the insufflation gas even though a temperature control system failure.

Normally, -control station 90, which is normally responsive to an electrical signal from the thermistor circuit 45 maintains the temperature of the insufflation gas within a normal range through delivery of more or less power to the electrical heating strip 40. However, as pointed out an electrical failure in either or both the thermistor circuit 45 or the control station 90 may overheat the insufflation gas delivered to the patient. In the system shown in FIG. 7 a normally passive device i.e. the thermal cutoff 46, which is located in series with the heating element 49 and proximate the heating element provides a fail-safe insufflator device that is independent of the temperature of the insufflation gas. Thus, the thermal cutoff 46 interrupts power to the electrical heating strip 40 heater 49 in response to the temperature proximate the electrical heater rather than the temperature of the insufflation gas thereby preventing accidental overheating of the insufflation gas.

While the thermal cutoff has been shown and described in conjunction with a control system for maintaining temperature control of the insufflation gas through a temperature measurement it is envisioned that the in some instance the thermal cutoff may be used without a control system since the thermal cutoff can limit insufflation gas overheating. Thermal cutoffs are commercially available and generally have an internal electrical conductor therein that switches from a closed condition to an open condition in response to a critical temperature of the thermal cutoff.

The thermal cutoff described herein is preferably of the type that once activated remains in an open condition thus preventing further use of the heater in the insufflator device, however, there may be conditions where a resetaable thermal cutoff may be used.

To appreciate the conventional operation of a gas conditioning trocar without the passive device reference should be made to FIGS. 1-4A.

FIG. 1 shows a partial cut away side view of a gas conditioning trocar for on-the-go heating and hydrating an insufflation gas during a medical procedure. Trocar 10 includes a cylindrical housing 12 having a cannula 26 on one end and a cover 13 on the opposite end. The cannula 26 comprises an elongated cylindrical tube for extending into a patient's body cavity.

Cylindrical housing 12 and an upper coaxial tube 21 form an annular chamber 11 within trocar 10. Annular chamber 11 comprises three parts, an upper annular plenum chamber 11a where insufflation fluids and insufflation gas are introduced, a central annular chamber 11c, which contains a conditioning media 20 for transporting the insufflation gas and a hydration fluid therethrough while bringing the insufflation gas to a conditioned state as it enters the lower annular plenum chamber 11b. From plenum chamber 11b the hydrated insufflation gas flows into cannula 26 through an annular outlet port 21a.

Connected to one side of housing 12 is a valve 18 for controlling the flow of insufflation gas into upper annular plenum chamber 11a and similarly connected to the opposite side of housing 12 is a further valve 19, which may be a check valve, to control the flow of hydration fluids into housing 12 as well as to prevent backflow of hydration fluids. While mechanical valves are shown other types of controls may be used, for example, fluidic controls may be used to control the delivery of fluids to the gas conditioning trocar. Mounted on the side of housing 12 is a junction box 16, which contains electrical leads 14 from a heater located in the conditioning media 20. Typically, the hydration fluid may be water, however, other fluids may be included with the water.

In operation of gas conditioning trocar 10 the insufflation gas and the hydration fluids are introduced into plenum chamber 11a before flowing in an axially direction through the conditioning media 20 in chamber 11c where the insufflation gas is hydrated and heated to the proper temperature for injection into the body cavity of a patient. As the insufflation gas and hydration fluids flow through the conditioning media 20 the conditioning media 20 allows the insufflation gas to be simultaneously hydrated and heated immediately prior to injection of the insufflation gas into the body cavity of a patient thus avoiding transport loses that may occur with remote hydration units.

Figure 2:
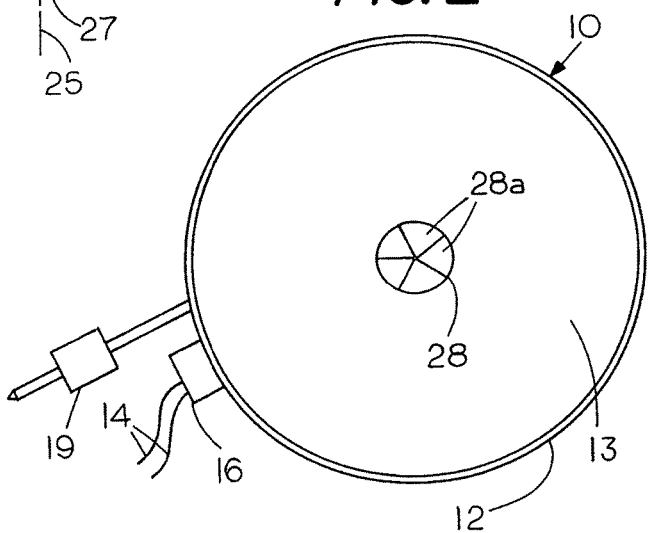
FIG. 2 is a top view of the trocar housing cover.

FIG. 2 shows a top view of the trocar housing 12 revealing an inlet instrument port 28, which is located in the center of housing 12. Extending across instrument port 28 is a closure comprising a plurality of segment shaped resilient flaps 28a that normally extend radially inward in tube 21 to block passage 21a and thereby inhibit or prevent backflow of hydrated insufflation gas therepast whether or not a surgical instrument is present in trocar 10. When a surgical instrument is inserted into trocar 10 the flaps 28a flex to allow the instrument to enter and pass through passage 21a in tube 21. Preferably, the flaps 28a are made of a resilient material such that they form a gas seal around the exterior surface of the surgical instrument therein to inhibit or prevent insufflation gas from escaping therepast when the surgical instrument is located in trocar 10. If the surgical instrument is withdrawn from tube 21 the flaps 28a return to the closed condition shown in FIG. 1 to thereby inhibit or prevent heated and hydrated insufflation gas (i.e., conditioned gas) from escaping through instrument inlet port 28. A further benefit is the flaps 28a may prevent contaminants from inadvertently entering trocar 10. While resilient flaps are shown comprising the closure other methods and means may be used to close off the instrument port to inhibit or prevent backflow of insufflation gas therepast.

In the example shown the on-the-go and in situ heating and hydrating of the insufflation gas takes place in conditioning media 20, which is located in the annular chamber in the gas conditioning trocar 10.

Figure 3:
FIG. 3 is a side view of a multilayer media in an unwound condition.

FIG. 3 shows a side view of an example of a strip of a conditioning media 20 for bringing an insufflation gas into a conditioned state. Media 20 comprises multiple layers i.e. a multilayer media, in an unwound or unassembled condition. In the example shown the materials of multilayer media 20 include a layer of gas transfer material comprising netting 32 and a layer of a fluid transferring material comprising hydrophilic material 30 with a heater assembly 34 extending therebetween. Heater assembly 34 includes a temperature sensor 22 on one end and a pair of electrical leads 14 on the opposite end for connection to a power source. Although three layers are shown the number and composition of the layers of material as well as the thickness of the layers may be modified according to the specific application. Temperature sensor 22 may be part of heater assembly 34 or may be separately mounted in trocar 20 to monitor the temperature of the insufflation gas before the insufflation gas is discharged from the trocar 20.

FIG. 4 shows the strip of multilayer media 20 comprises a plurality of three layers of materials 30, 32 and 34, which are wound into a spiral configuration that may be inserted into the annular chamber in trocar 10. In the spiral configuration state, as shown in FIG. 4, the hydrating liquid may be brought into proximity of a heater assembly 34 through an absorbing action of a hydrophilic layer 30 in media 20. The absorbing action allows distribution of the hydrating liquid proximate the heater assembly 34. Similarly, a porous netting 32 allows the insufflation gas to flow therethrough so the gas can be brought into proximity of the heater assembly 34 to enable the insufflation gas to be brought to a conditioned state.

FIG. 4A is a cross sectional view of the spirally wound media 20 taken along lines 4A-4A of FIG. 4 revealing the multiple layers comprising the conditioned media 20.

In order to secure the multilayer media 20 in the housing 12 the multilayer media 20 may be wound into a diameter slightly larger than the diameter of housing 12 to enable one to friction fit multilayer media 20 in housing 12. If frictional forces are used to hold multilayer media 20 the multilayer media should be selected to offer sufficiently low flow resistance so that the insufflation gas flow flowing thereto will not displace the multilayer media 20.

Alternatively, multilayer media 20 could be adhesively secured to housing 12. It is noted that an advantage of the friction fit of multilayer media 20 in housing 12 is that the friction fit eliminates the need for an adhesive to hold multilayer media 20 in place. An adhesive may interfere with the flow of insufflation gas from one layer of multilayer media 20 to another. An alternate method of holding the multilayer media 20 in position may be to use a radial supports in chamber 11b to support the lower end of multilayer media 20. Other methods of securing the multilayer media 20 may also be used to maintain the multilayer media 20 in position to deliver hydrated insufflation gas to annular outlet port 29.

To minimize the pressure drop through netting 32 two or more layers of netting may be placed proximate each other to increase the porosity though the netting. That is, netting 32 provides flow passages for the insufflation gas to flow from plenum chamber 11a to plenum chamber 11b without undue but sufficient resistance so that the hydration fluid and the hydration fluid can be maintained in proximity to enable hydration to take place. A suitable netting 32, for example, is a bi-planar polypropylene netting having properties including a density of 11 strands per inch and a thickness of 0.030 inches (e.g., Delstar, Middleton, Del.).

Multilayer media 20 includes at least one layer of a liquid transfer media, which for example may be a hydrophilic media 30, which readily absorbs and retains a volume of hydration fluid provided to plenum chamber 11a. While other types of materials, for example wicking materials, may be used to deliver the hydration fluid into proximity of the heater assembly 34 the hydrophilic media 30 brings the hydration fluid in close proximity to both heater assembly 34 and the insufflation gas through an absorbing action. Similarly, two or more layers of hydrophilic material may be used to bring the hydration liquid proximate the heater assembly.

Hydrophilic media 30 is thin and flexible so that it is easily wound in a spiral configuration with the other layers of multilayer media 20 as shown in FIG. 4. Although many types of hydrophilic material are useable a typical suitable hydrophilic media 30 is cellulose which is commercially available from Knowlton, Watertown, N.Y. having the following characteristics: a basis weight of 91-99 pounds/3000 ft$^2$ and a thickness of about 0.028-0.034 inches.

The multilayer media 20 includes a heater assembly 34, which comprises an elongated flexible heating element that has external electrical leads 44 for connecting to a source of electrical power. The heater assembly 34 is thin and flexible such that when it is sandwiched between the hydrophilic layer 30 and the layer of netting 32 the combination can be wound into a spiral configuration that can be inserted within housing 12. An advantage of the spiraled configuration is that it provides a continuous extended area for heating and hydration of the insufflation gas, i.e., the insufflation flow path is long. In the preferred embodiment, heater assembly 34, for example, is a resistance heating element made of etched copper foil coated with a layer of polyimide. Another layer of polyimide coats the foil surface. The coating of polyimide waterproofs heater assembly 34 to prevent heater assembly 34 from contacting the hydration fluid or hydrated gas that may result in an electrical short.

One end of heater assembly 34 may terminate with a temperature sensor 22 for measuring the temperate of the insufflation gas in the gas conditioning trocar 10. When heater assembly 34 is layered with the other materials of multilayer media 20 and friction fit into housing 12, temperature sensor 22, for example a thermistor, detects the temperature of the conditioned insufflation gas at lower plenum chamber 11b. A heater control, not shown, can increase or decrease the power supplied to heater assembly 34 to ensure that the insufflation gas is kept at the proper temperature for injection into a body cavity. The opposite end of heater assembly 34 terminates with electrical leads 14 which can be connected to a power source. When heater assembly 34 is layered with netting 32 and hydrophilic media 30 and assembled into a spiral configuration, electrical leads 14 extend beyond the multilayer media 20. Thus, when the multilayer media 20 is placed in housing 12, the electrical leads 14 extend beyond housing 12 for connection to a source of electrical power as shown in FIG. 1.

In the preferred embodiment, multilayer media 20 is assembled into a spiral configuration (FIG. 4) although other configurations may be used. An advantage of the spiral configuration is that the hydrating fluid and insufflation gas are brought in to close proximity to the heater assembly 34 as they flow from annular plenum chamber 11a to annular plenum chamber 11b. Although an annular conditioning media 20 which extends from side to side is shown the gas conditioning media may take other shapes or forms which allow the insufflation gas to be conditioned within the trocar. For example, only a portion of the annular chamber in the trocar may be used for the conditioning of the gas.

A further benefit and advantage of use of a multilayer media is that multilayer media 20 can more easily be assembled in a flat condition and subsequently wound into a spiral configuration for insertion into the annular chamber of the trocar 10. While a spiral configuration is a suitable configuration for conditioning media 20, one may want to assemble conditioning media 20 in other configurations that provide for extended contact between the heater and the insufflation gas so the insufflation gas can be brought in to a conditioned state. While a conditioning media 20 has been described as a preferred embodiment it will be evident that other methods and materials may be used to condition an unconditioned gas in the trocar.

Referring to FIG. 1, an elongated cylindrical passages 21a and 26a extend along a central axis 25 of trocar 10. Passages 21a and 26a are of adequate diameter to simultaneously house a surgical instrument and allow a flow insufflation gas without undue fluid resistance thereto.

Trocar 10 may include a closure such as a hinged flap 24, which is normally held in a closed position by a spring 24a to prevent backflow of bodily fluids or other materials from the patient's body cavity. Flap 24 opens in response to a medical instrument being inserted into passages 26a. It is noted that while flap 24 is the preferred embodiment, other methods or structures may be used to prevent backflow.

In operation, the gas conditioning trocar 10 the electrical leads 14 receive electrical power from a power source (not shown) and cannula 26 extends into the patient's body cavity. Typically, an insufflation gas flows from a gas source (not shown) in to plenum chamber 11a through valve 18. Meanwhile a volume of hydrating fluid (not shown) flows into plenum chamber 11a through valve 19. The hydrophilic media 30 of multilayer media brings the hydrating fluid in close proximity to heater assembly 34. Hydrating fluid is supplied to hydration inlet chamber 11a in order to maintain the preferred hydration range before and during the surgical procedure.

The insufflation gas flows from inlet 18 into plenum chamber 11a and therefrom through the porous netting where the insufflation gas is heated and hydrated. More specifically, the unconditioned insufflation gas flows into upper plenum chamber 11a and then flows downward through multilayer media 20 where the insufflation gas is heated and hydrated.

The temperature sensor 22 in heater assembly 34 detects the temperature of the insufflation gas and transmits a signal representing the temperature of the insufflation gas to a control circuit (not shown). The control circuit sends a signal to control the heat delivered from heater assembly 34. The control can be used to maintain the insufflation gas in the preferred temperature range before and during the surgical procedure.

The conditioned insufflation gas flows from lower plenum chamber 11b into passage 26a through annular outlet port 29. A surgical instrument may be passed through instrument inlet 28, into passage 21a and, through cannula 26 and out the end 27 of cannula 26. The instrument may be withdrawn and other instruments may be used in a similar fashion throughout the procedure. As such, the delivery of conditioned insufflation gas and the use of surgical instruments may occur simultaneously without adversely affecting or interfering with each other.

In summary, in one example the invention is a gas conditioning trocar 10 for in situ heating and hydrating an insufflation gas during a medical procedure and in another the conditioning or insufflator device is located upstream of the trocar. In one example the gas conditioning trocar comprises a housing 12 having a hydration chamber 11 containing a heater assembly 34 sandwiched between a layer of hydrophilic material and a layer of porous netting for heating and hydrating the insufflation gas before the insufflation gas is injected into body cavity. While layers of material are shown to comprise media 20 other configurations besides layers of materials may be used to bring the insufflation gas to a conditioned state in trocar 10.

The invention is also a method of heating and hydrating insufflation gas in a trocar 10 during an endoscopic surgical procedure including the steps of extending the cannula 26 into a body cavity by flowing unconditioned insufflation gas to the trocar 10 for in situ conditioning of the insufflation gas which may include either heating and/or hydrating the insufflation gas in the trocar 10 to bring the insufflation gas to a conditioned state, and then delivering the conditioned insufflation gas to a body cavity by flowing the insufflation gas through the cannula 26.

We claim:

1. A fail-safe gas conditioning trocar for delivering a conditioned insufflation gas into a body cavity of a patient while preventing overheating of the conditioned insufflation gas therein comprising: a housing having an instrument port, a gas conditioning chamber and an inlet for receiving an unconditioned insufflation gas; a cannula; a gas conditioning media located in said trocar comprising a hydration member; an electrical heater comprising: an electrically insulating backing strip that supports a thermistor circuit, wherein the thermistor circuit comprises a set of thermistors located along the electrical heater on opposite edges of the electrical heater and an elongated flexible heating element extending along an interior portion of the electrical heater, the elongated flexible heating element located between the set of thermistors, the elongated flexible heating element having a set of electrical leads connected to a source of electrical power; the thermistor circuit responsive to a temperature, of the insufflation gas flowing through said gas conditioning media; a control station responsive to the thermistor circuit for maintaining the temperature of the insufflation gas through delivery of more or less power to the electrical heater in response to a signal from the thermistor circuit to thereby maintain the insufflation gas in a thermally conditioned state; and a one-piece thermal cutoff located directly on a leg of the the elongated flexible heating element and in series with the elongated flexible heating element, said thermal cutoff having a first lead connected to one end of the electrical heater and a second lead connected to another end of the electrical heater to form an electrical conducting path through the elongated flexible heating element and the thermal cutoff, said thermal cutoff responsive to an excessive temperature proximate the electrical heater to mechanically interrupt current to the electrical heater to prevent overheating the insufflation gas in the trocar due to an errant temperature condition proximate the electrical heater rather than a sensed temperature of the insufflation gas.

2. The fail-safe gas conditioning trocar of claim 1 wherein the gas conditioning media comprises a spiral wound gas hydration member and the electrical heater comprises a spiral wound heating element with a face of the hydration member and a face of the heating element extending alongside each other as the insufflation gas flows therebetween.

3. The fail-safe gas conditioning trocar of claim 1 wherein the thermal cutoff is located less than ⅓ the distance from a distal end of the electrical heater.

4. The fail-safe gas conditioning trocar of claim 1 wherein the control station includes an alarm for alerting an operator that the insufflation gas has exceeded an entry temperature.

5. The fail-safe gas conditioning trocar of claim 1 wherein the control station includes an alarm for alerting an operator that the temperature of the electrical heater has exceeded a threshold temperature which is in excess of the temperature of the insufflation gas.

6. The fail-safe gas conditioning trocar of claim 1 wherein the thermal cutoff is located within a spiral wound porous media.

7. The fail-safe gas conditioning trocar of claim 1 wherein the thermistor circuit and the electrical heater are located in a spiral configuration extending radially outward from the cannula centrally located in said gas conditioning trocar.

8. The fail-safe gas conditioning trocar of claim 1 wherein said hydration member and said electrical heater are circumferentially positioned around the instrument port.

9. A fail-safe insufflator device for delivering a conditioned insufflation gas into a body cavity of a patient while preventing overheating of the insufflation gas during a medical procedure comprising: a housing; a chamber located in said housing; a gas conditioning media located in said chamber; an electrical heater in the chamber for heating the insufflation gas by flowing the insufflation gas through the conditioning media before delivery of the insufflation gas to the body cavity of the patient, said electrical heater having an electrically insulating backing strip that supports a thermistor circuit, wherein the thermistor circuit comprises a set of thermistors located along the electrical heater on opposite edges of the electrical heater and a heating element extending along an interior portion of the electrical heater, the heating element located between the set of thermistors; a one-piece thermal cutoff located directly on a leg of the heating element and in series with the heating element, said thermal cutoff interrupting current through the heating element of the electrical heater due to a temperature condition proximate the electrical heater rather than a sensed temperature of the insufflation gas to prevent the insufflation gas from becoming overheated; and a cannula for directing the conditioned insufflation gas into the body cavity of the patient.

10. The fail-safe insufflator device of claim 9 including a control station for interrupting current to the electrical heater in the event of a measured temperature proximate the electrical heater exceeds a safe level.

11. The fail-safe insufflator of device claim 9 wherein the electrical heater is a spiral wound heater and the thermal cutoff is closer to a distal end of the spiral wound heater than to the proximal end of the spiral wound heater.

12. The fail-safe insufflator device of claim 9 wherein the fail-safe insufflator device comprises gas conditioning trocar having a gas insufflation port and an electrical port.

13. An insufflation device for delivering a conditioned insufflation gas into a body cavity of a patient while preventing overheating of an insufflation gas therein comprising: a cannula configured to extend into the body cavity of a patient; a housing having an instrument port, a gas conditioning chamber and an inlet for receiving an unconditioned insufflation gas; a gas conditioning media located in said housing comprising a hydration member for hydration of the unconditioned insufflation gas and an elongated electrical heating strip having a heating element for heating of the unconditioned insufflation gas and electrically insulating backing strip that supports a thermistor circuit, wherein the thermistor circuit comprises a set of thermistors located along the electrical heating strip on opposite edges of the electrical heating strip, said heating element extending in a lengthwise direction along an interior portion said electrical heating strip and located between the set of thermistors; the thermistor circuit responsive to a temperature of the insufflation gas flowing through said gas conditioning media; a control station responsive to the thermistor circuit for maintaining the temperature of the insufflation gas through delivery of more or less power to the electrical heating strip in response to a signal from the thermistor circuit to thereby maintain the insufflation gas in a thermally conditioned state; a one-piece solid thermal cutoff located directly on a leg of the heating element and in series with said heating element to form an electrical conducting path through the heating element and the thermal cutoff, said thermal cutoff responsive to a hostile temperature proximate the heating element to mechanically interrupt current to the electrical heater due to an errant temperature condition proximate the electrical heating strip rather than the sensed temperature of the insufflation gas to prevent overheating the insufflation gas in the insufflation device; and a cannula passage for directing the conditioned insufflation gas through to deliver the conditioned insufflation gas to the body cavity of the patient.

14. An insufflation apparatus for delivering a conditioned insufflation gas into a body cavity of a patient while preventing overheating of the insufflation gas during a medical procedure comprising: a cannula configured to extend into the body cavity of a patient; a housing having a chamber; a gas conditioning media; an electrical heater in the chamber for heating the insufflation gas by flowing the insufflation gas through the gas conditioning media; the electrical heater comprising: an electrically insulating backing strip that supports a thermistor circuit, wherein the thermistor circuit comprises a set of thermistors located along the electrical heater on opposite edges of the electrical heater and a heating element extending along an interior portion of the electrical heater, the elongated flexible heating element located between the set of thermistors, and a one-piece reset-able thermal cutoff located directly on a leg of the heating element and in series with the heating element, said thermal cutoff interrupting current to the electrical heater and the heating element in response to a temperature condition proximate the electrical heater; and a cannula passage for directing the heated insufflation gas through to deliver the heated insufflation gas to the body cavity of the patient.

15. A method of maintaining the temperature of an insufflation gas for delivery into a body cavity of a patient while preventing the insufflation gas from overheating comprising: extending a cannula into the body cavity of a patient; directing the insufflation gas into a chamber of a trocar having an electrical heater, the electrical heather comprising: an electrically insulating backing strip that supports a thermistor circuit, wherein the thermistor circuit comprises a set of thermistors located along the electrical heater on opposite edges of the electrical heater and a flexible heating element extending along an interior portion of the electrical heater, the heating element located between the set of thermistors; heating the insufflation gas in the chamber of the trocar as it passes through the flexible heating element of the electrical heater; measuring the temperature of the insufflation gas proximate the electrical heater with a temperature sensor; controlling the temperature of the insufflation gas based on the temperature at the temperature sensor with a temperature control station; directing an electrical current through a passive, one-piece thermal cutoff located directly on a leg of the flexible heating element and in series with the flexible heating element, said thermal cutoff forming an electrical conducting path through the electrical heater; disabling the electrical heater by interrupting current to the electrical heater due to an errant temperature proximate the electrical heater rather than a sensed temperature of the insufflation gas in the event the controlling the temperature of the insufflation gas based on a temperature sensor signal fails to prevent overheating the insufflation gas; and delivering the heated insufflation gas into the body cavity of the patient by flowing the insufflation gas through the cannula.

16. The method of claim 15 wherein the method of disabling the electrical heater comprises placing the passive, one-piece thermal cutoff proximate the electrical heater.

17. The method of claim 16 including placing the thermal cutoff in a system having a temperature control system responsive to an electrical fault signal from the temperature sensor.

18. The method of claim 16 including the step of spiral winding the electrical heater around a porous media in a gas condition trocar.

19. The method of claim 18 including the step of placing the thermal cutoff on an end of the electrical heater that is radially closer to a central instrument tube in the trocar.

* * * * *